(12) United States Patent
Strnad et al.

(10) Patent No.: US 6,296,665 B1
(45) Date of Patent: Oct. 2, 2001

(54) METHOD AND APPARATUS FOR SPINAL FIXATION

(75) Inventors: Lee A. Strnad; Kirk J. Bailey, both of Andover, NJ (US)

(73) Assignee: Electro-Biology, Inc., Parsippany, NJ (US)

( * ) Notice: Subject to any disclaimer, the term of this patent is extended or adjusted under 35 U.S.C. 154(b) by 0 days.

(21) Appl. No.: 09/531,847

(22) Filed: Mar. 20, 2000

(51) Int. Cl.⁷ .................................................... A61F 2/44
(52) U.S. Cl. ................................................... 623/17.16
(58) Field of Search ............................. 623/17.16, 17.15

(56) References Cited

U.S. PATENT DOCUMENTS

| | | |
|---|---|---|
| 3,987,499 | 10/1976 | Scharbach et al. ............... 3/1.91 |
| 4,309,777 | 1/1982 | Patil .................................. 3/1.91 |
| 4,401,112 | 8/1983 | Rezaian . |
| 4,553,273 | 11/1985 | Wui . |
| 4,657,550 | 4/1987 | Daher . |
| 4,932,975 | 6/1990 | Main et al. . |
| 4,946,378 | 8/1990 | Hirayama et al. . |
| 4,997,432 | 3/1991 | Keller ............................... 606/61 |
| 5,062,850 | 11/1991 | MacMillan et al. . |
| 5,192,327 | 3/1993 | Brantigan . |
| 5,236,460 | 8/1993 | Barber . |
| 5,306,308 | 4/1994 | Gross et al. . |
| 5,336,223 | 8/1994 | Rogers .............................. 606/61 |
| 5,360,430 | 11/1994 | Lin .................................... 606/61 |
| 5,370,697 | 12/1994 | Baumgartner . |
| 5,423,816 | 6/1995 | Lin .................................... 606/61 |
| 5,458,641 | 10/1995 | Ramirez Jimenez . |
| 5,534,030 | 7/1996 | Navarro et al. . |
| 5,562,738 | 10/1996 | Boyd et al. . |
| 5,571,192 | 11/1996 | Schonhoffer . |
| 5,683,464 | 11/1997 | Wagner et al. . |
| 5,683,465 | 11/1997 | Shinn et al. . |
| 5,702,453 | 12/1997 | Rabbe et al. . |
| 5,723,013 | * 3/1998 | Jeanson et al. ................. 623/17.16 |
| 5,755,798 | 5/1998 | Papavero et al. . |
| 5,800,550 | 9/1998 | Sertich . |
| 5,888,223 | 3/1999 | Bray, Jr. . |
| 5,888,227 | * 3/1999 | Cottle ............................. 623/17.16 |
| 5,893,889 | 4/1999 | Harrington . |
| 5,895,428 | 4/1999 | Berry . |
| 5,972,031 | * 10/1999 | Biedermann et al. ........... 623/17.16 |
| 6,015,436 | * 1/2000 | Schonhoffer .................... 623/17.16 |
| 6,019,792 | * 2/2000 | Cauthen .......................... 623/17.16 |

\* cited by examiner

Primary Examiner—Paul J. Hirsch
(74) Attorney, Agent, or Firm—Harness, Dickey & Pierce P.L.C.

(57) ABSTRACT

An apparatus for spinal fixation has a longitudinally extending core which provides structural integrity and allows for bone growth along the center column of the spine. The apparatus for spinal fixation further includes upper and lower platform members radially extending from upper and lower ends, respectively, of the core. The platform members each include a plurality of radially extending arms which define substantially triangular openings therebetween. The openings permit bone ingrowth therethrough to the space between the upper and lower platform members which is interrupted only by the core.

22 Claims, 4 Drawing Sheets

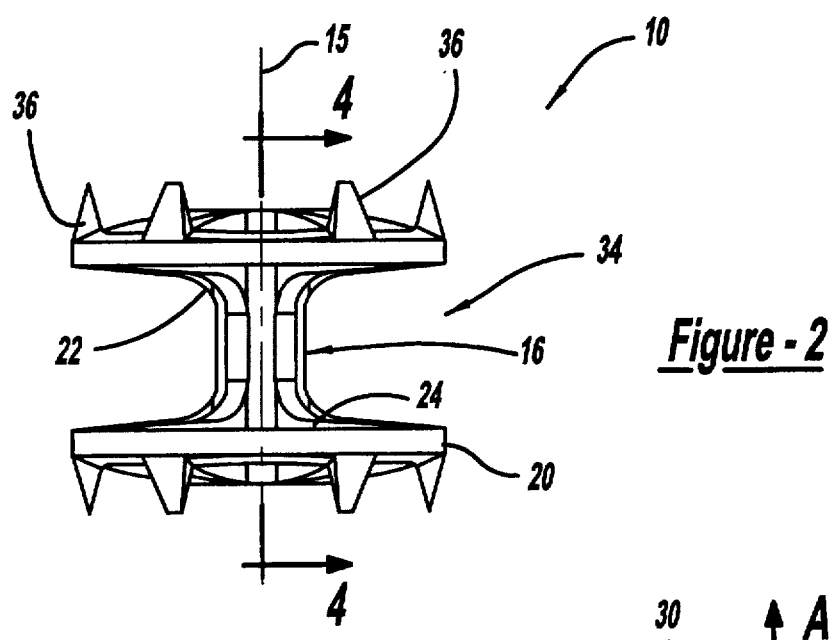
*Figure - 2*
*Figure - 3*
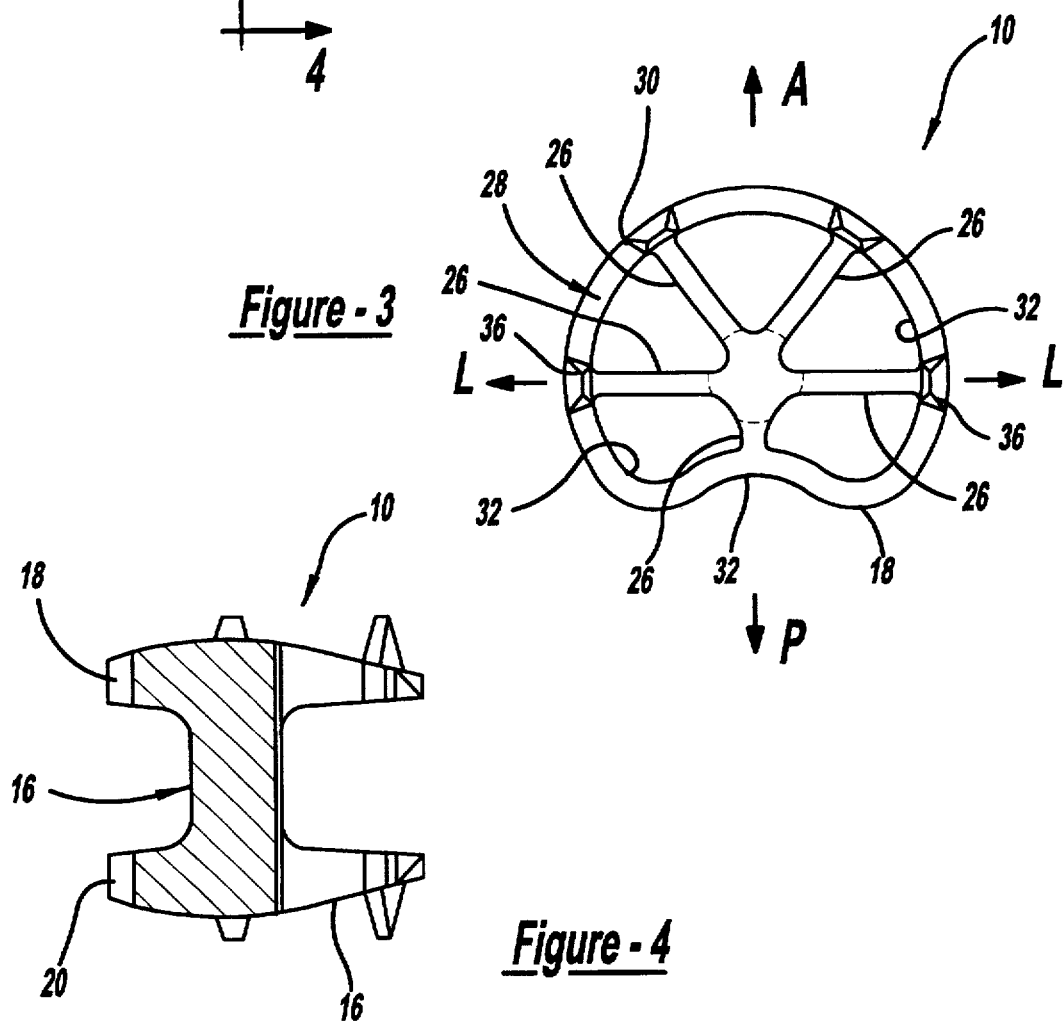
*Figure - 4*

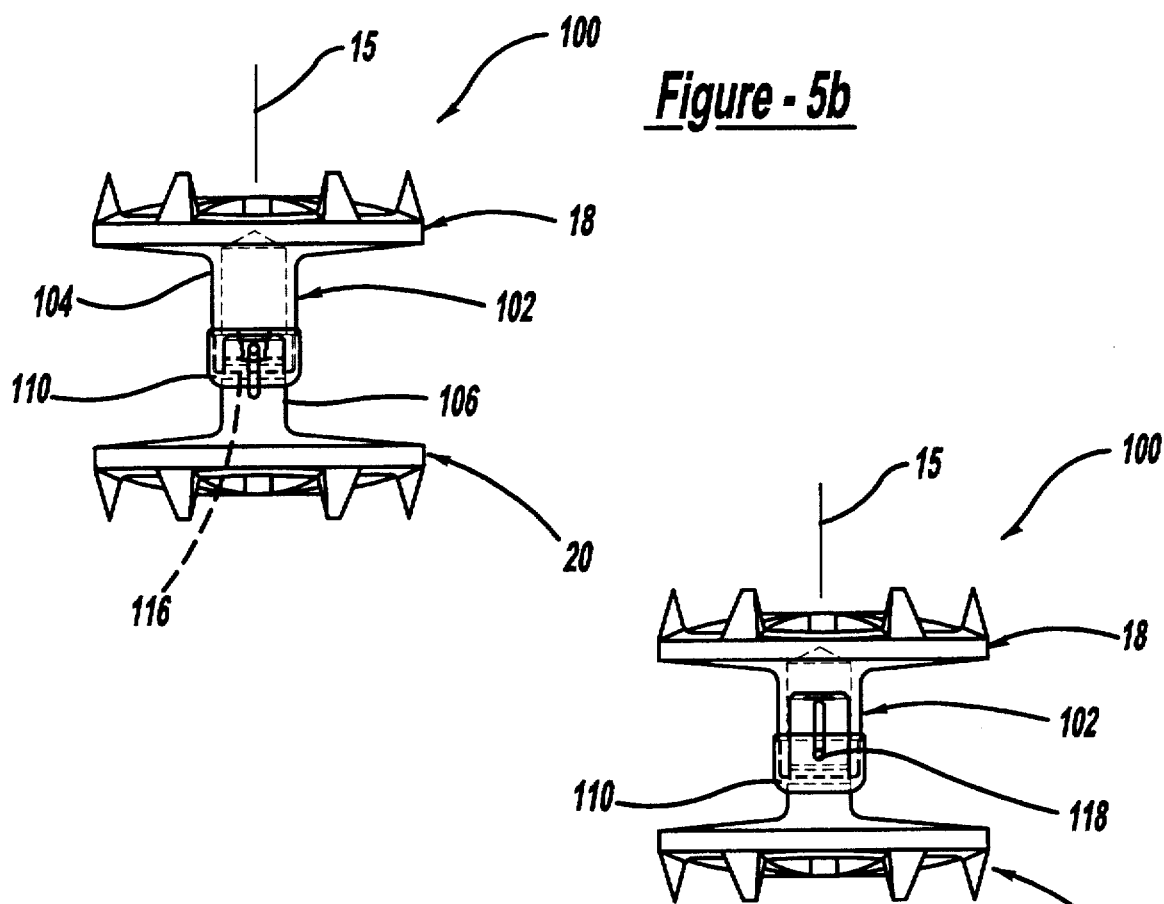
*Figure - 5b*
*Figure - 5a*
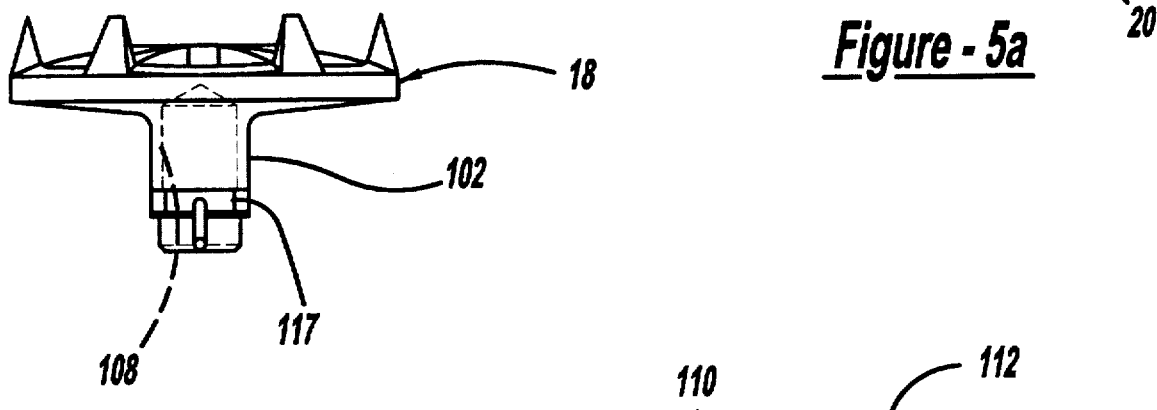
*Figure - 6*
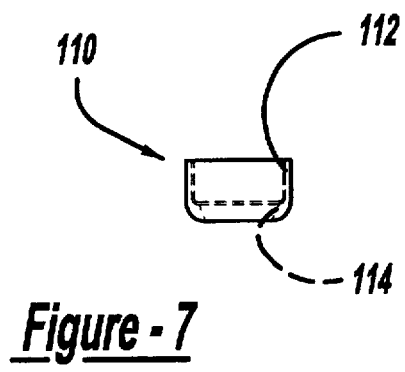
*Figure - 7*

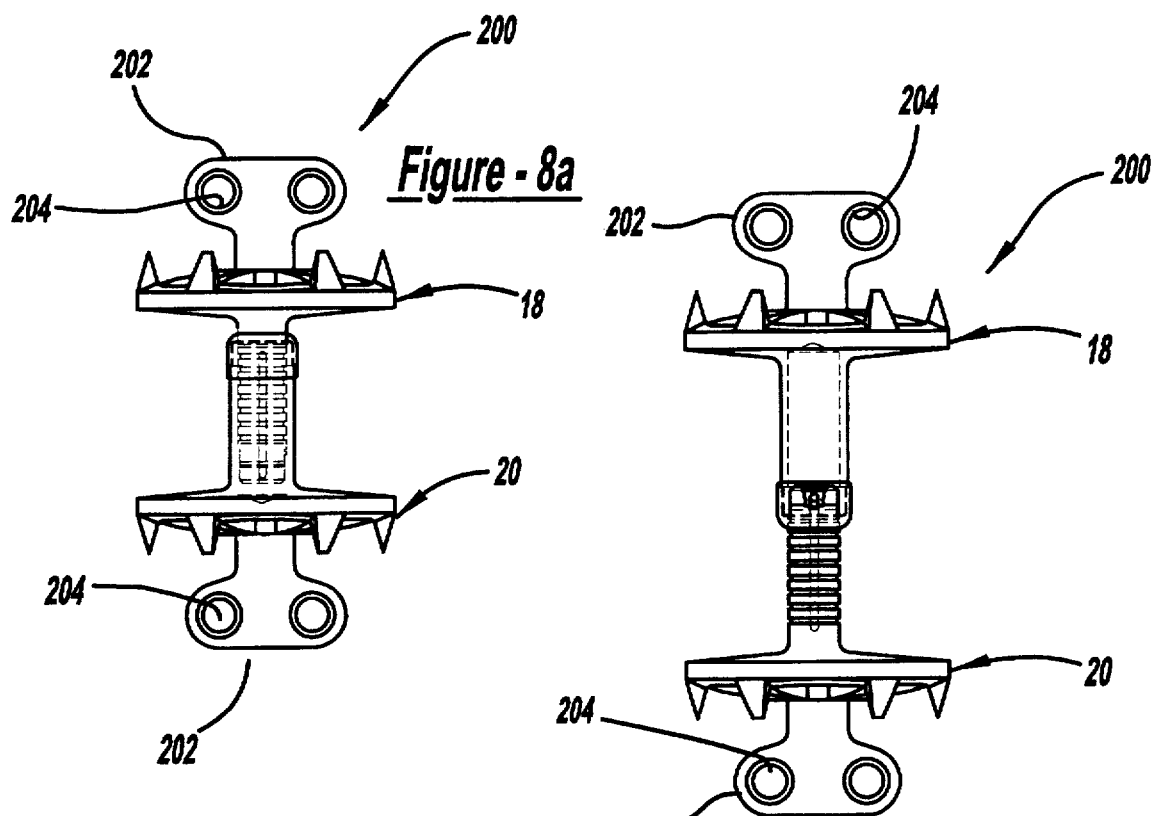
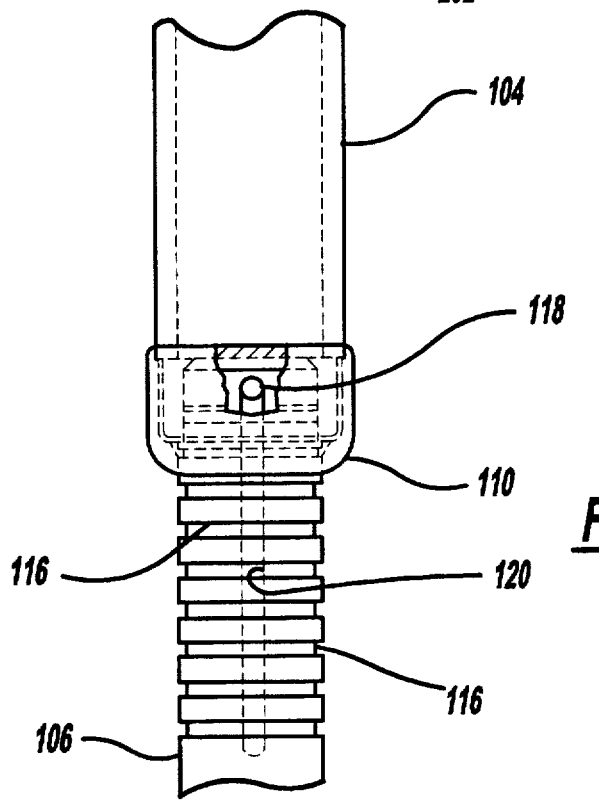

METHOD AND APPARATUS FOR SPINAL FIXATION

BACKGROUND OF THE INVENTION

1. Field of the Invention

The present invention relates generally to an orthopedic surgical procedure, and more particularly to a method and an apparatus for spinal fixation.

2. Description of the Related Art

In various orthopedic surgical procedures, it is necessary to secure portions of a spinal column in a relatively fixed relationship. This need is often a result of disease, damage or congenital deformation. Heretofore, surgeons have used various types of bone and bone substitutes to help stabilize the spinal column and promote fusion. It is also known to insert an implant or prosthesis in place of a disk or vertebral body that has been removed.

While known devices for spinal fixation have proven to be effective in various applications to support the spinal column and promote fusion, they nevertheless can be the subject of certain improvements. In this regard, conventional spinal fixation devices do not provide flexible structural support allowing for adequate load sharing. Additionally, many spinal fixation devices rely on cutting through adjacent endplates for proper anchoring which may not be suitable for all applications. Thus, it would be advantageous to provide an apparatus for spinal fixation and related method that improve upon known devices.

SUMMARY OF THE PRESENT INVENTION

According to one aspect of the present invention, an apparatus for spinal fixation is provided including a longitudinally extending core and a pair of platform members which radially extend relative to an axis defined by the core.

An advantage of the present invention is to provide an apparatus for spinal fixation and a related method which enhances bone fusion and minimizes stress shielding.

A related advantage of the present invention is to provide an apparatus for spinal fixation and a related method that provides a flexible structural support which allows load sharing in all directions.

Another advantage of the present invention is to provide an apparatus for spinal fixation that is easily implanted.

Another advantage of the present invention is to provide an apparatus for spinal fixation and a related method that do not cut through adjacent endplates of the vertebral body.

Another advantage of the present invention is to provide an apparatus for spinal fixation that may be quickly and easily adjusted in length.

Another advantage of the present invention is to provide an apparatus for spinal fixation and a related method that promote the fusion rate of bone.

A related advantage of the present invention is to provide an apparatus for spinal fixation and a related method that provide electrical current for enhancing bone growth.

Another advantage of the present invention is to provide an apparatus for spinal fixation and a related method which allow a first degree of flexibility during spinal column flexion and a second, smaller degree of flexibility during spinal column extension.

Another advantage of the present invention is to provide an apparatus for spinal fixation and a related method which substantially allows unobstructed post-operative x-ray vision of the bone fusion site between adjacent vertebral bodies.

Additional advantages and features of the present invention will become apparent from the following description and appended claims, taken in conjunction with the accompanying drawings.

In one particular form, the particular invention provides an apparatus for spinal fixation. The apparatus includes a core, an upper platform and a lower platform member. The core longitudinally extends along an axis. The upper platform member radially extends about the axis. The lower platform member radially extends about the axis. At least one of the upper and lower platform members includes a plurality of radially extending arms defining openings therebetween for permitting bone ingrowth.

BRIEF DESCRIPTION OF THE DRAWINGS

FIG. 2 is an enlarged side view of an apparatus for spinal fixation according to the teachings of the preferred embodiment of the present invention shown removed from the exemplary environment of FIGS. 1A–1C for purposes of illustration.

FIG. 3 is a top view of the apparatus for spinal fixation according to the teachings of the preferred embodiment of the present invention.

FIG. 4 is a sectional view taken along the line 4—4 of FIG. 2.

FIGS. 5A and 5B are side views of an apparatus for spinal fixation constructed according to the teachings of a second preferred embodiment of the present invention shown in compressed and expanded conditions, respectively.

FIG. 6 is a side view of the upper half of the apparatus for spinal fixation of the second preferred embodiment of the present invention.

FIG. 7 is a side view of a lock nut of the apparatus for spinal fixation of the second preferred embodiment shown removed from the apparatus for purposes of illustration.

FIGS. 8A and 8B are side views of an apparatus for spinal fixation constructed according to the teachings of a third embodiment of the present invention shown in compressed and expanded conditions, respectively.

FIG. 9 is an enlarged side view of the core of the apparatus of the third preferred embodiment of the present invention.

DETAILED DESCRIPTION OF THE PREFERRED EMBODIMENTS

The following description of the preferred embodiments of the present invention is merely exemplary in nature and is in no way intended to limit the invention or its application or uses. As will become apparent below, the first and second embodiments are primarily intended for intervertebral spinal fusion. The third preferred embodiment is primarily intended for vertebral body replacement.

Figure 1A:
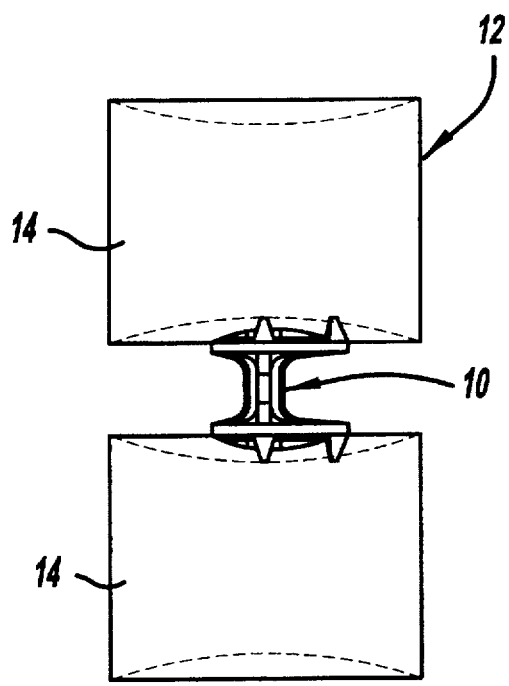
FIGS. 1A, 1B, and 1C illustrate a pair of an apparatuses for spinal fixation constructed according to the teachings of the first preferred embodiment of the present invention and shown in operative association with a human spinal column.
Figure 1B:
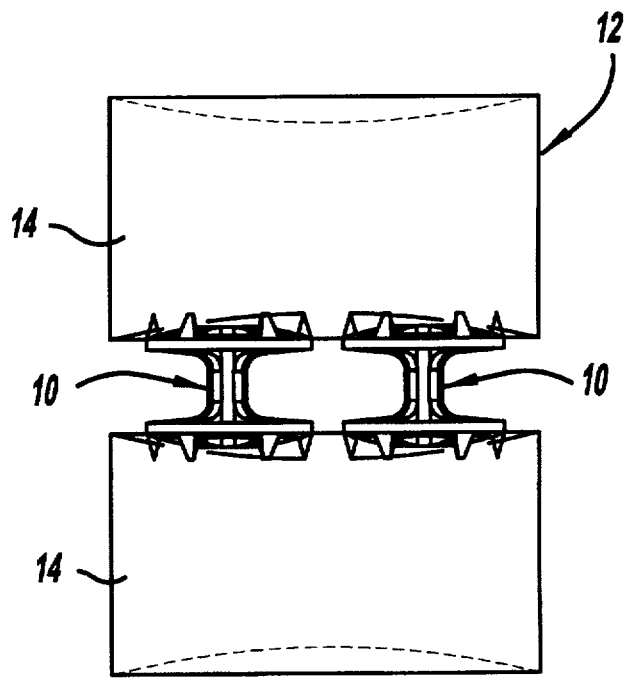
Figure 1C:
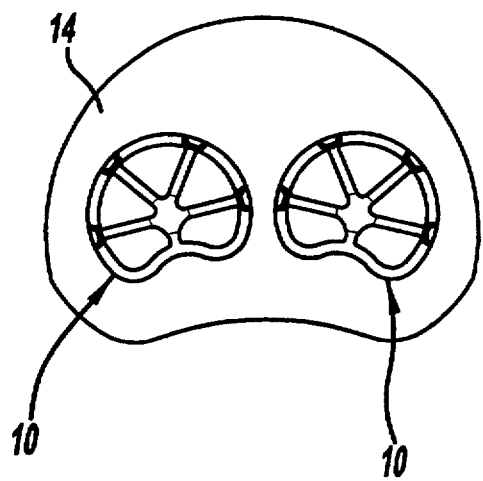

Referring initially to FIGS. 1A through 4 wherein like reference numerals designate identical or corresponding parts throughout the several views, an apparatus for spinal fixation constructed according to a first preferred embodiment of the present invention is illustrated. The apparatus is generally identified at reference numeral 10. In FIGS. 1A, 1B, and 1C, a pair of substantially identical apparatuses for spinal fixation 10 are shown operative associated with a portion of a human spinal column 12. Each apparatus for spinal fixation 10 is positioned between adjacent vertebra 14 within the disk space, the disk (not shown) having been removed in a conventional manner. A spinal fixation device of the type intended to be used in the manner shown in FIGS. 1A–1C is often referred to as a spinal cage. While the apparatuses for spinal fixation 10 is shown in FIGS. 1A through 1C in pairs, it will be appreciated that either one apparatus 10 or three or more apparatuses 10 may be employed within the scope of the present invention.

The structure and function of the apparatus for spinal fixation 10 of the first preferred embodiment of the present invention will be described with particular reference to FIGS. 2 through 4. The apparatus 10 is illustrated to generally include a core or column 16, a first platform member or upper platform member 18 and a second platform member or lower platform member 20. As illustrated, the apparatus 10 includes a single core 16. In alternative applications, multiple cores 16 may be incorporated. For example, it may be desired to combine the pair of apparatuses shown in the environmental views to a single structure having a pair of cores 16.

In the first preferred embodiment, the core 16 is solid and capable of withstanding significant compression loads generated within the spinal column 12. The core 16 defines a longitudinal axis 15 and is generally cylindrical in shape. In one application, the core 16 has a radius of approximately 2.0 mm. The core 16 is preferably formed to include a plurality of longitudinal extending grooves for accommodating increased axial loads.

In the preferred embodiment, the core 16 has a generally circular cross section. Alternatively, the core 16 may include a cross section with a plurality of flat sides. For example, the cross section of the core 16 may alternatively be hexagonal or rectangular. It will be understood that the cross section of the core can be altered to vary flexibility of the apparatus 10 in a directionally dependent manner (e.g., flextion, extension).

The upper and lower platform members 18 and 20 radially extend from upper and lower ends 22, 24, respectively, of the core 16. In the first preferred embodiment, the upper and lower platform members 18 and 20 are substantially identical. For this reason, only the upper platform member 18 will be described in further detail. The upper platform member 18 includes a plurality of arms 26 radially extending from the core 16. The ends of the arms 26 are connected by a circumferential rim 28. In one application, the circumferential rim 28 has a width of approximately 1.5 mm and the radially extending arms 26 have a width of approximately 1.0 mm. The circumferential rim 28 defines a generally kidney-shape having a circular portion 30 and recessed portion 32.

In the exemplary embodiment illustrated, the plurality of arms 26 is illustrated to include five arms 26. However, it will be understood that the particular number of arms 26 is a matter of design choice. Explaining further, the upper and lower platform members 20 can be formed to include either a lesser or greater number of arms 26.

Adjacent arms of the plurality of arms 26 define openings or slots 32. The openings 32 permit bone ingrowth into a space 34 between the upper and lower platform members 18 and 20. Bone ingrowth is facilitated by the relatively large openings 32 compared to the narrow width of the arms 26. As illustrated, the openings 32 adjacent the circular portion 30 of the rim 28 are generally triangular in shape. In certain applications, it may be desired to apply an electric current to the apparatus to further enhance bone ingrowth.

At least one of the arms 26 extends in a generally anterior direction, indicated by arrow A. As shown most particularly in FIG. 3, two arms 26 extend generally in the anterior direction. One arm is shown extending in a generally posterior direction, indicated by arrow P. An additional two arms extend generally in lateral directions, indicated by arrows L. The arms 26 which extend in the generally anterior direction and generally in the lateral direction are significantly longer than the arm 26 extending in the posterior direction due to the kidney-shape of the outer rim 28. Due to cantilevered nature of the arms 26, the generally anteriorly extending arms 26 and the generally laterally extending arms 26 define larger moment arms than the generally posteriorly extending arms 26. As a result, the apparatus for spinal fixation 10 of the present invention opposes flexion and lateral bending of the spinal column 12 to less of a degree than it opposes extension of the spinal column 12.

The upper platform member 18 is further shown to include a plurality of prongs or teeth 36 which generally extend in a direction parallel to the longitudinal axis 15. The prongs or teeth 36 terminate at a point and are intended to pierce the endplates of the adjacent vertebral bodies 14 to eliminate any migration of the apparatus 10. As illustrated in the exemplary embodiment, the prongs 36 are four in number and are located on the outer rim 28 adjacent the ends of four of the arms 26.

In the preferred embodiment, an upper surface of the upper platform member 18, which is defined by the rim 28 and arms 26, is partially spherical in shape. This configuration mates with the geometry of an adjacent vertebral body 14. In this manner, the apparatus 10 contacts a larger surface area of the adjacent vertebral body end plate to further facilitate load sharing.

The apparatus for spinal fixation 10 of the present invention is preferably unitarily constructed of a material suitable for implantation into the human body. One suitable material for the apparatus 10 is a Ti-6 Al-4 V ELI alloy. However, it will be understood that alternative materials may be incorporated.

With reference to FIGS. 5A, 5B and 6, an apparatus for spinal fixation 100 constructed according to the teachings of a second preferred embodiment of the present invention is illustrated. It will be understood that with the exception of the core 16, the apparatus for spinal fixation 100 of the second preferred embodiment is identical to the apparatus for spinal fixation 10 of the first preferred embodiment. For this reason, common reference numerals are used in the drawings to identify corresponding components between the first and second preferred embodiments.

As will be further appreciated below, the core 102 of the apparatus 100 shares a common locking mechanism with the core of the apparatus 200 of the third preferred embodiment. The core 102 of the apparatus 100 may be extended along the longitudinal axis 15 defined by the core 16 between a compressed position (see FIG. 5A) and an expanded position (see FIG. 5B). The core 102 is shown to preferably include a first portion or upper portion 104 carried by the upper platform member 18 and a second portion or lower portion 106 carried by the lower platform member 20. As shown, the upper portion 104 is hollow and defines an opening 108 for telescopically receiving the lower portion 106.

The lower portion 106 of the core 102 rotatably carries a lock nut 110. The lock nut 110 includes an internally threaded portion 108 that meshingly engages an outer diameter of the upper portion 104. In the preferred embodiment, the lock nut 110 further includes a tapered portion 114 having an inner diameter that tapers. The outer diameter of the upper portion 104 has a corresponding taper such that threaded advancement of the lock nut 110 partially crushes the diameter of the upper portion 104 to thereby fix the relative positions between the upper and lower platform members 18 and 20 after the apparatus 100 is positioned in its correct anatomical position. As shown, the tapered portion 114 engages a reduced diameter locking groove 116 of the lower portion 106.

As illustrated, the upper portion 104 of the core 102 is formed to include an inwardly extending rib or locking ring 117 (shown most particularly in FIG. 6). The locking ring 117 engages locking groove 116. In this manner, the adjustable core 102 is strengthened to accommodate increased axial loads.

In the preferred embodiment, the apparatus 100 has a height range of approximately 2 mm. In a first application, the apparatus 100 has a height of approximately 12 mm in the compressed state and a height of approximately 14 mm in the expanded state. In a second application, the apparatus 100 has a height of approximately 10 mm in the compressed state and a height of approximately 12 mm in the expanded state. In a third application, the apparatus 100 has a height of approximately 14 mm in the compressed state and a height of approximately 16 mm in the expanded state. Alternate height ranges are anticipated within the scope of the present invention.

The apparatus 200 is preferably shown to further include a pin 118 carried by the upper portion 104. The pin 118 is disposed in a slot 120 in the lower portion 106. The pin 118 cooperates with the slot 120 to allow relative telescopic movement between the upper and lower portions 104 and 106 while preventing the upper and lower portions 104 and 106 from becoming disconnected.

Turning now to FIG. 7, an apparatus for spinal fixation 200 constructed in accordance with the teachings of a third preferred embodiment of the present invention is illustrated. The apparatus for spinal fixation 200 of the third preferred embodiment is substantially similar to the apparatus for spinal fixation of the second preferred embodiment 100 of the first preferred embodiment. For this reason, common reference numerals have been used to identify substantially identical elements.

The apparatus for spinal implantation of the third preferred 200 embodiment is specifically intended to replace a complete vertebral body and adjacent vertebral disks. In most applications in which a vertebral body is being replaced, it will be desired to incorporate a longitudinally extendable core 16. However, it will be understood by those skilled in the art that the apparatus for spinal fixation 200 of the third preferred embodiment of the present invention may alternatively include a fixed length core 16.

In the preferred embodiment, the apparatus 200 has a height range of approximately 15 mm. In a first application, the apparatus 200 has a height of approximately 45 mm in a fully compressed state (see FIG. 8A) and has a height of approximately 60 mm in a fully expanded state (see FIG. 8B). In a second application, the apparatus 200 has a height of approximately 30 mm in a fully compressed state and has a height of approximately 45 mm in a fully expanded state. In a third application, the apparatus 200 has a height of approximately 60 mm in a fully compressed state and has a height of approximately 75 mm in a fully expanded state. Alternate height ranges are anticipated within the scope of the present invention.

The lower portion 106 of the apparatus 200 is formed to include a plurality of reduced diameter grooves 116. The plurality of grooves 116 provides various points along the length of the lower portion 106 at which the lock nut 110 can be secured. In this manner, the apparatus 200 can be extended to various selected lengths.

The apparatus 200 is further shown to include a pair of extended plates 202. A first extended plate 202 upwardly extends from the upper platform member 18 and a second extended plate 202 downwardly extends from the lower platform member 20. The plates 202 each define a pair of apertures 204. The apertures 204 are adapted to receive cortical or bicortical screws (not shown) for attachment to the vertebral bodies 12. In this manner, structural integrity of the apparatus 200 is enhanced.

The implantation of an apparatus constructed in accordance with the teachings of the present invention will be described with reference to the apparatus 100 of the second preferred embodiment. It will be understood that implantation of the apparatus 10 of the first preferred embodiment is substantially identical but for elimination of any height adjustment of the core 16. Similarly, implantation of the apparatus 200 of the third preferred embodiment of the present invention is substantially identical but for the removal of a vertebral body and an additional disk.

The apparatus 100 is primarily intended for anterior insertion. However, the teachings of the subject invention may also be applied posteriorly or laterally. The apparatus for spinal fixation 100 is inserted with the aid of simple distraction of adjacent vertebral bodies and removal of the disk material therebetween. Such distraction may be accomplished in any conventional manner. Since the apparatus 100 is not threaded into the vertebral bodies 14, operating time is reduced and integrity of the adjacent end plates is not adversely effected.

Prior to implantation, it may be desired to pack the space 34 between the upper and lower platform members 18 and 20 with bone material (not shown) to facilitate bone ingrowth. The bone material may be held in place by an outer sleeve (not shown) which is slipped around the apparatus 200. While not shown, it will be understood that the outer sleeve is preferably made of a bioresorbable material such as LactoSorb® which is commercially available through the assignee of this application. When the apparatus of the second preferred embodiment is in place, it is distracted to the proper height and the lock nut 108 is tightened until relative telescopic movement between the upper and lower portions 102 and 104 is prevented.

The apparatuses 10, 100 and 200 of the present invention each substantially allow unobstructed, post-operative, x-ray vision of the bore fusion site between adjacent vertebral bodies.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. An apparatus for spinal fixation comprising:
   a core longitudinally extending along an axis;
   an upper platform member radially extending about the axis; and
   a lower platform member radially extending about the axis;
   at least one of the upper and lower platform members including a plurality of radially extending arms defining openings therebetween for permitting bone ingrowth.

2. The apparatus for spinal fixation of claim 1, wherein both the upper and lower platform members include a plurality of radially extending arms.

3. The apparatus for spinal fixation of claim 1, wherein the plurality of radially extending arms includes at least a first arm extending in a generally posterior direction and at least a second arm extending in a generally anterior direction.

4. The apparatus for spinal fixation of claim 3, wherein the second arm is substantially longer than the first arm.

5. The apparatus for spinal fixation of claim 1, wherein the platform member of the at least one of the upper and lower platform members includes an outer rim interconnecting an end of each of the plurality of radially extending arms.

6. The apparatus for spinal fixation of claim 1, wherein the at least one of the upper and lower platform members is substantially kidney-shaped.

7. The apparatus for spinal fixation of claim 1, wherein a space between the upper and lower platform members is interrupted only by the core.

8. The apparatus for spinal fixation of claim 1, wherein the core is extendable along the axis.

9. The apparatus for spinal fixation of claim 8, wherein the core includes first and second telescopically related portions.

10. The apparatus for spinal fixation of claim 8, wherein a first portion of the core telescopically receives a second portion of the core, the first portion including an inwardly extending locking ring engaging a locking groove formed on the second platform.

11. An apparatus for spinal fixation comprising:
a core longitudinally extending along an axis; and
an upper platform member and a lower platform member, the upper and lower platform members radially extending from an upper end and a lower end of the core, the platform members both radially extending about the core and including a plurality of radially extending arms, both the platform members further including a rim connecting an end of each arm of the plurality of arms.

12. The apparatus for spinal fixation of claim 11, wherein the rims of both the upper and lower platform members have a kidney shape.

13. The apparatus for spinal fixation of claim 11, wherein the plurality of radially extending arms includes at least a first arm extending in a generally posterior direction and at least a second arm extending in a generally anterior direction.

14. The apparatus for spinal fixation of claim 13, wherein the second arm is substantially longer than the first arm.

15. The apparatus for spinal fixation of claim 11, wherein a space between the upper and lower platform members is interrupted only by the core.

16. The apparatus for spinal fixation of claim 11, wherein the core is extendable along the axis.

17. The apparatus for spinal fixation of claim 16, wherein the core includes first and second telescopically related portions.

18. The apparatus for spinal fixation of claim 16, wherein a first portion of the core telescopically receives a second portion of the core, the first portion including an inwardly extending locking ring engaging a locking groove formed on the second platform.

19. A method of stabilizing a spinal column comprising the steps of:
selecting an apparatus including a core extending along a longitudinal axis and upper and lower platforms members radially extending from an upper end and a lower end of the longitudinal axis, respectively, both of the upper and lower platforms including a plurality of radially extending arms, adjacent arms defining openings;
implanting the apparatus into a spinal column; and
opposing flexion of the spinal column with at least a first of the plurality of radially extending arms; and
opposing extension of the spinal column with at least a second of the plurality of radially extending arms.

20. The method of stabilizing a spinal column of claim 19, further comprising the step of permitting bone ingrowth through the openings.

21. The method of stabilizing a spinal column of claim 19, further comprising the step of expanding the core along the longitudinal axis.

22. The method of stabilizing a spinal column of claim 19, wherein the first of the plurality of radially extending arms is substantially longer than the second of the plurality of radially extending arms.

* * * * *